(12) United States Patent
Koh

(10) Patent No.: US 7,672,716 B1
(45) Date of Patent: Mar. 2, 2010

(54) QT-BASED SYSTEM AND METHOD FOR DETECTING AND DISTINGUISHING DILATED CARDIOMYOPATHY AND HEART FAILURE USING AN IMPLANTABLE MEDICAL DEVICE

(75) Inventor: Steve Koh, South Pasadena, CA (US)

(73) Assignee: Pacesetter, Inc., Sylmar, CA (US)

( * ) Notice: Subject to any disclaimer, the term of this patent is extended or adjusted under 35 U.S.C. 154(b) by 799 days.

(21) Appl. No.: 11/397,066

(22) Filed: Apr. 3, 2006

(51) Int. Cl.
A61B 5/0452 (2006.01)

(52) U.S. Cl. ...................................... 600/515
(58) Field of Classification Search ................. 600/509, 600/513–516
See application file for complete search history.

(56) References Cited

U.S. PATENT DOCUMENTS

| | | | |
|---|---|---|---|
| 5,328,460 A | 7/1994 | Lord et al. | 604/67 |
| 5,340,361 A | 8/1994 | Sholder | 607/24 |
| 5,560,368 A | 10/1996 | Berger | 128/703 |
| 6,249,705 B1 | 6/2001 | Snell | 607/59 |
| 6,324,423 B1 * | 11/2001 | Callahan et al. | 600/516 |
| 6,361,503 B1 * | 3/2002 | Starobin et al. | 600/508 |
| 6,438,408 B1 | 8/2002 | Mulligan et al. | 600/510 |
| 6,438,409 B1 * | 8/2002 | Malik et al. | 600/512 |
| 6,572,557 B2 | 6/2003 | Tchou et al. | 600/483 |
| 6,645,153 B2 | 11/2003 | Kroll et al. | 600/481 |
| 2002/0143265 A1 * | 10/2002 | Ackerman et al. | 600/515 |
| 2003/0032936 A1 * | 2/2003 | Lederman | 604/507 |
| 2004/0077962 A1 | 4/2004 | Kroll | 600/513 |
| 2005/0010123 A1 * | 1/2005 | Charuvastra et al. | 600/515 |

OTHER PUBLICATIONS

Jose Luis Alonso, M.D., et al., "Dynamics of Ventricular Repolarization in Patients with Dilated Cardiomyopathy Versus Healthy Subjects," *Annals of Noninvasive Electrocardiology*, Apr. 2005; vol. 10, No. 2, pp. 121-128.

* cited by examiner

Primary Examiner—George R Evanisko
Assistant Examiner—Joseph M Dietrich

(57) ABSTRACT

Techniques are provided for detecting dilated cardiomyopathy within a patient using a pacemaker or other implantable medical device. Briefly, values representative of QT duration and QT dispersion are detected within the patient and then the risk of dilated cardiomyopathy is evaluated based on the values of QT duration and QT dispersion. In one particular example, the implanted device calculates an index representative of the extent to which individual QT duration and QT dispersion values deviate from a daily mean. The device then compares the index against a threshold indicative of a substantial likelihood of the presence of dilated cardiomyopathy within the patient. Additional techniques described herein relate to distinguishing dilated cardiomyopathy from heart failure within patients that may have one or both conditions.

10 Claims, 8 Drawing Sheets

FIG. 4A

EXEMPLARY QT-BASED EVALUATION TECHNIQUE USING DAILY HISTOGRAMS

152 — DETECT QT DURATION AND QT DISPERSION BY:
- SENSING THE INTRACARDIAC ELECTROGRAM (IEGM) OF THE PATIENT;
- IDENTIFYING QT INTERVALS WITHIN THE IEGM; AND
- CALCULATING QT DURATION AND QT DISPERSION BASED ON THE QT INTERVALS

154 — DETERMINE QT DURATION AND QT DISPERSION DAILY MEAN VALUES BY:
- GENERATING A QT DISPERSION HISTOGRAM ($H_{QT-DISPERSION}$) BASED ON A PLURALITY OF QT DISPERSION VALUES DETECTED OVER ONE DAY;
- GENERATING A QT DURATION HISTOGRAM ($H_{QT-DURATION}$) BASED ON A PLURALITY OF QT DURATION VALUES DETECTED OVER ONE DAY; AND
- CALCULATING A QT DISPERSION DAILY MEAN AND A QT DURATION DAILY MEAN USING THE HISTOGRAMS

160 — QUANTIFY THE DEVIATION IN QT DURATION AND QT DISPERSION FROM THEIR RESPECTIVE DAILY MEANS BY:
- SUBTRACTING THE QT DISPERSION DAILY MEAN FROM EACH BIN VALUE IN THE QT DISPERSION HISTOGRAM ($H_{QT-DISPERSION}$);
- SUBTRACTING THE QT DURATION DAILY MEAN FROM EACH BIN VALUE IN THE QT DURATION HISTOGRAM ($H_{QT-DURATION}$) AND MULTIPLYING EACH OF THE BIN VALUES IN THE QT DURATION HISTORGRAM ($H_{QT-DURATION}$) BY A CORRESPONDING QT DURATION HISTOGRAM ($H_{QT-DURATION}$ BIN COUNT; AND
- SUBTRACTING THE QT DISPERSION DAILY MEAN FROM EACH BIN VALUE IN THE QT DISPERSION HISTOGRAM ($H_{QT-DISPERSION}$) AND MULTIPLYING EACH OF THE BIN VALUES IN THE QT DISPERSION HISTOGRAM ($H_{QT-DISPERSION}$) BY A CORRESPONDING QT DISPERSION HISTOGRAM ($H_{QT-DISPERSION}$) BIN COUNT

QT-BASED SYSTEM AND METHOD FOR DETECTING AND DISTINGUISHING DILATED CARDIOMYOPATHY AND HEART FAILURE USING AN IMPLANTABLE MEDICAL DEVICE

FIELD OF THE INVENTION

The invention generally relates to implantable medical devices, such as pacemakers or implantable cardioverter/defibrillators (ICDs), and in particular to techniques for detecting and distinguishing cardiomyopathy and heart failure within a patient in which a medical device is implanted.

BACKGROUND OF THE INVENTION

Cardiomyopathy relates to the deterioration of the cardiac muscle of the heart wall. The most common form is dilated cardiomyopathy wherein the heart, particularly the left ventricle, is enlarged and weakened. Often the cause is unknown. This is referred to as idiopathic dilated cardiomyopathy (IDC). IDC and other forms of cardiomyopathy can lead to heart failure, which is a debilitating condition in which abnormal function of the heart leads to inadequate blood flow to fulfill the needs of the tissues and organs of the body. Typically, the heart loses propulsive power because the cardiac muscle loses capacity to stretch and contract. Often, the ventricles do not adequately fill with blood between heartbeats and the valves regulating blood flow become leaky, allowing regurgitation or back-flow of blood. The impairment of arterial circulation deprives vital organs of oxygen and nutrients. A particularly severe form of heart failure is congestive heart failure (CHF) wherein the weak pumping of the heart leads to build-up of fluids in the lungs and other organs and tissues. CHF is often fatal. Hence, cardiomyopathy increases the risk of mortality since it can lead to heart failure. In addition, cardiomyopathy can trigger various life-threatening arrhythmias such as ventricular fibrillation, which can result in sudden cardiac death. As can be appreciated, cardiomyopathy is a potentially serious condition that should be detected and treated as early as possible.

Many patients at risk of cardiomyopathy or heart failure, particularly the elderly, have pacemaker or ICDs implanted therein, or are candidates for such devices. Various techniques have been developed to detect heart failure within a patient using a pacemaker or ICD. See, for example: U.S. patent application Ser. No. 11/100,008, of Koh et al., filed May 11, 2004, entitled "System And Method For Evaluating Heart Failure Using An Implantable Medical Device Based On Heart Rate During Patient Activity"; U.S. patent application Ser. No. 11/100,008, of Kil et al., entitled "System And Method For Detecting Heart Failure And Pulmonary Edema Based On Ventricular End-Diastolic Pressure Using An Implantable Medical Device", filed Apr. 5, 2005; U.S. patent application Ser. No. 11/014,276, of Min et al., entitled "System And Method For Predicting Heart Failure Based On Ventricular End-Diastolic Volume/Pressure Using An Implantable Medical Device", filed Dec. 15, 2004; U.S. patent application Ser. No. 10/810,437, of Bornzin et al., entitled "System and Method for Evaluating Heart Failure Based on Ventricular End-Diastolic Volume Using an Implantable Medical Device," filed Mar. 26, 2004; U.S. patent application Ser. No. 10/346,809, of Min et al., entitled "System and Method for Monitoring Cardiac Function via Cardiac Sounds Using an Implantable Cardiac Stimulation Device," filed Jan. 17, 2003; and U.S. patent application Ser. No. 10/792,305, filed Mar. 2, 2004, entitled "System And Method For Diagnosing And Tracking Congestive Heart Failure Based On The Periodicity Of Cheyne-Stokes Respiration Using An Implantable Medical Device". See also: U.S. Pat. No. 6,572,557, to Tchou, et al., entitled "System and Method for Monitoring Progression of Cardiac Disease State Using Physiologic Sensors." U.S. Pat. No. 6,645,153, to Kroll et al., entitled "System and Method for Evaluating Risk of Mortality Due To Congestive Heart Failure Using Physiologic Sensors", and U.S. Pat. No. 6,438,408 to Mulligan et al., entitled "Implantable Medical Device For Monitoring Congestive Heart Failure."

However, heretofore, it does not appear that any viable techniques have been developed for detecting dilated cardiomyopathy using an implanted device, at least before the myopathy progresses to heart failure. Accordingly, it would be highly desirable to provide techniques for detecting and tracking dilated cardiomyopathy using a pacemaker or other implantable medical device, and it is to this end that aspects of the invention are directed. Early detection of dilated cardiomyopathy via an implanted device could significantly improve the patient's long term prognosis. Note, though, that many patients with heart failure do not have dilated cardiomyopathy. Conversely, many patients with dilated cardiomyopathy do not have heart failure. Other patients have both. Accordingly, it would also be desirable to provide techniques for use by an implanted device for distinguishing between dilated cardiomyopathy and heart failure, and it is to this end that other aspects of the invention are directed.

SUMMARY

Techniques are provided for detecting and distinguishing dilated cardiomyopathy and heart failure within a patient using an implantable medical device. In one example, values representative of QT duration and QT dispersion are detected within the patient and then an increased risk of dilated cardiomyopathy is detected based on the values of QT duration and QT dispersion. Herein, QT generally represents the time interval between a ventricular depolarization and a corresponding ventricular repolarization of the heart of the patient. Ventricular depolarization is manifest as a QRS-complex within the intracardiac electrogram (IEGM) of the patient. Ventricular repolarization is manifest as a T-wave in the IEGM. Hence, QT duration generally refers to the time interval between the QRS-complex and the T-wave. QT dispersion (i.e. QTd) generally refers to the difference between a maximum measured QT value and a minimum measured QT value when the same QT interval is measured using different pairs of electrodes. In one particular example, the implanted device calculates an index ($QT_{INDEX}$) representative of an extent to which individual QT duration and QT dispersion values deviate from daily mean values. The device then compares the index against a threshold indicative of a substantial likelihood of the presence of dilated cardiomyopathy to thereby detect the condition. Herein, dilated cardiomyopathy is deemed to be "detected" if the device determines that there is a substantial likelihood of the presence of dilated cardiomyopathy within the patient.

In a preferred embodiment, the implanted device calculates $QT_{INDEX}$ by: determining a daily mean of QT duration values and a daily mean of QT dispersion values; quantifying an amount of deviation in QT duration and in QT dispersion values from their respective daily means; and then combining the amount of deviation and dispersion to yield $QT_{INDEX}$. The daily mean of QT duration values and the daily mean of QT dispersion values may be determined, for example, using histogram-based techniques by generating a QT dispersion histogram ($H_{QT\text{-}dispersion}$) based on a plurality of QT dispersion values detected over one day; generating a QT duration histogram ($H_{QT\text{-}duration}$) based on a plurality of QT duration values detected over one day; and then calculating the QT dispersion daily mean and the QT duration daily mean using the histograms. The amount of deviation in QT duration and in QT dispersion values from their respective daily means may be quantified, for example, by: subtracting the QT dispersion daily mean from each bin value in the QT dispersion histogram ($H_{QT\text{-}dispersion}$); subtracting the QT duration daily mean from each bin value in the QT duration histogram ($H_{QT\text{-}duration}$) and multiplying each of the bin values in the QT duration histogram ($H_{QT\text{-}duration}$) by a corresponding QT duration histogram ($H_{QT\text{-}duration}$) bin count; and then subtracting the QT dispersion daily mean from each bin value in the QT dispersion histogram ($H_{QT\text{-}dispersion}$) and multiplying each of the bin values in the QT dispersion histogram ($H_{QT\text{-}dispersion}$) by a corresponding QT dispersion histogram ($H_{QT\text{-}dispersion}$) bin count. The resulting bin values within the QT duration histogram ($H_{QT\text{-}duration}$) are summed together with the resulting bin values within the QT dispersion histogram ($H_{QT\text{-}duration}$) to yield $QT_{INDEX}$ for comparison against the detection threshold. The use of bins in this manner reduces the amount of memory required to implement the technique, as compared to techniques that would individually store data pertaining to each QT interval.

Preferably, the implanted device is also capable of detecting heart failure based, for example, on a reduction in R-R variability, i.e. a decrease in the variation of the duration between consecutive ventricular depolarization events. By assessing both R-R variability and QT duration/QT dispersion, the implanted device distinguishes between cardiomyopathy and heart failure. More specifically, if R-R variability is normal but QT duration and QT dispersion are both elevated, then the device determines that the patient has dilated cardiomyopathy without heart failure. If R-R variability is reduced and QT duration and QT dispersion are elevated, then the device determines that the patient has both dilated cardiomyopathy and heart failure. If R-R variability is reduced but QT duration and QT dispersion are normal, then the device determines that the patient has heart failure without dilated cardiomyopathy. Finally, if R-R variability is normal and QT duration and QT dispersion are also normal, the device determines that the patient has neither dilated cardiomyopathy nor heart failure. Note, though, that continuous tracking of R-R variability can be a burden on device resources. Accordingly, in at least some embodiments, R-R variability is not continuously assessed until after an increase in QT duration or QT dispersion is detected. In other words, once possible cardiomyopathy is detected based on QT intervals, then R-R variability is also tracked to determine if the cardiomyopathy progresses to heart failure.

Once either dilated cardiomyopathy or heart failure has been detected, appropriate therapy may be automatically provided by the implanted device, such as cardiac resynchronization therapy (CRT) or drug therapy (if an implantable drug pump is provided with appropriate medications.) In addition, suitable warning signals are preferably generated to alert the patient and/or the physician. The physician may then conduct otherwise conventional medical tests to determine if the patient does indeed have cardiomyopathy and/or heart failure. Warnings may be delivered either via an implanted warning device (if so equipped) or via an external bedside monitor or other external warning system. Diagnostic information representative of cardiomyopathy and/or heart failure is also preferably stored for subsequent review by the physician. Suitable diagnostic information may also be displayed via the bedside monitor.

Thus, various techniques are provided for use with implantable medical devices for detecting and distinguishing dilated cardiomyopathy and heart failure and for triggering appropriate therapy or warning signals.

BRIEF DESCRIPTION OF THE DRAWINGS

The above and further features, advantages and benefits of the invention will be apparent upon consideration of the present description taken in conjunction with the accompanying drawings, in which:

FIGS. 4A and 4B depict a flow diagram illustrating a particular procedure performed in accordance with the general technique of FIG. 1 for detecting and evaluating dilated cardiomyopathy based on QT intervals, which exploits histogram-based techniques;

DETAILED DESCRIPTION OF THE PREFERRED EMBODIMENTS

The following description includes the best mode presently contemplated for practicing the invention. This description is not to be taken in a limiting sense but is made merely to describe general principles of the invention. The scope of the invention should be ascertained with reference to the issued claims. In the description of the invention that follows, like numerals or reference designators are used to refer to like parts or elements throughout.

Overview of Implantable System

Figure 1:
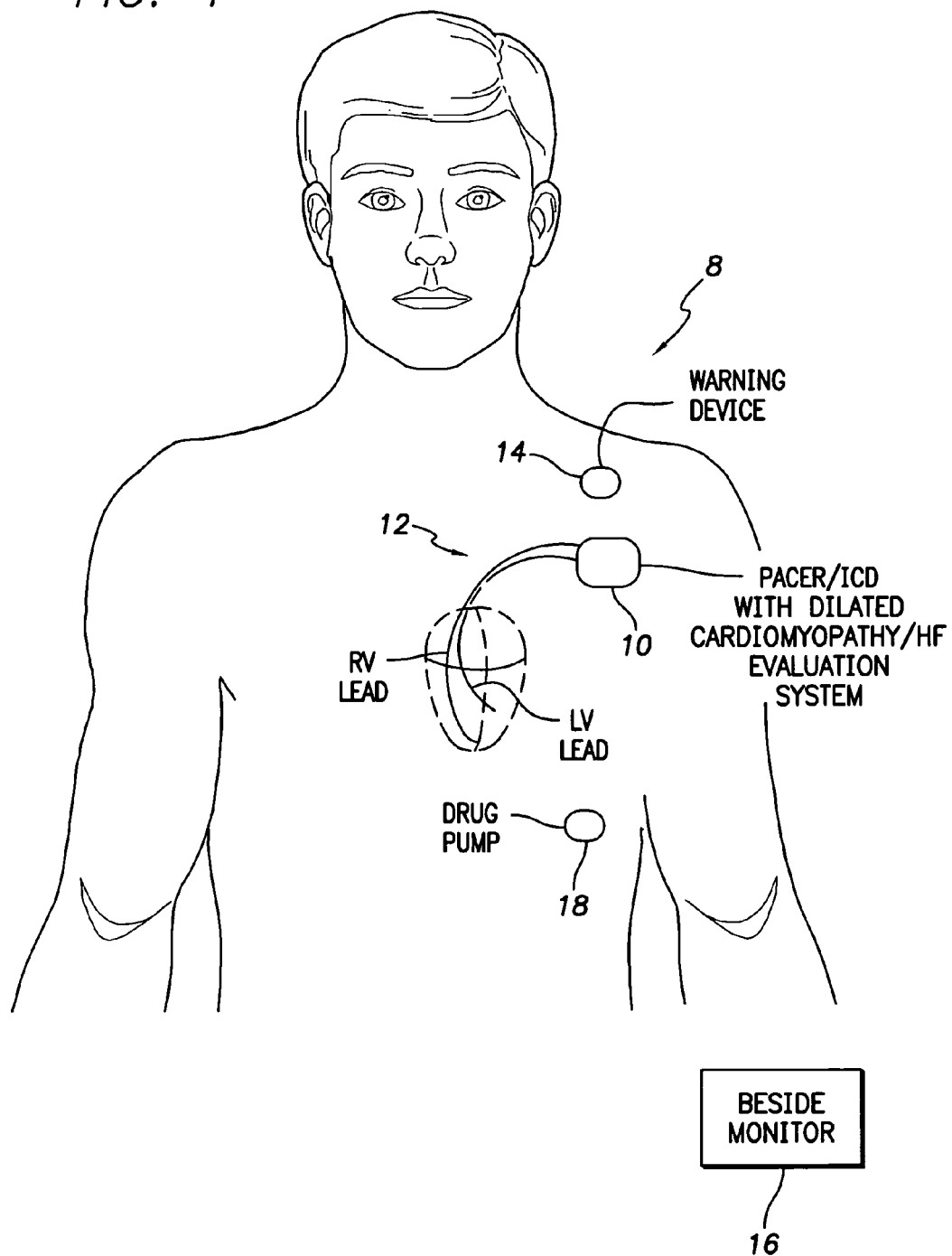
FIG. 1 illustrates pertinent components of an implantable medical system having a pacemaker or ICD capable of detecting distinguishing dilated cardiomyopathy and heart failure within the patient and further capable of delivering therapy or warning signals in response thereto.
Figure 7:
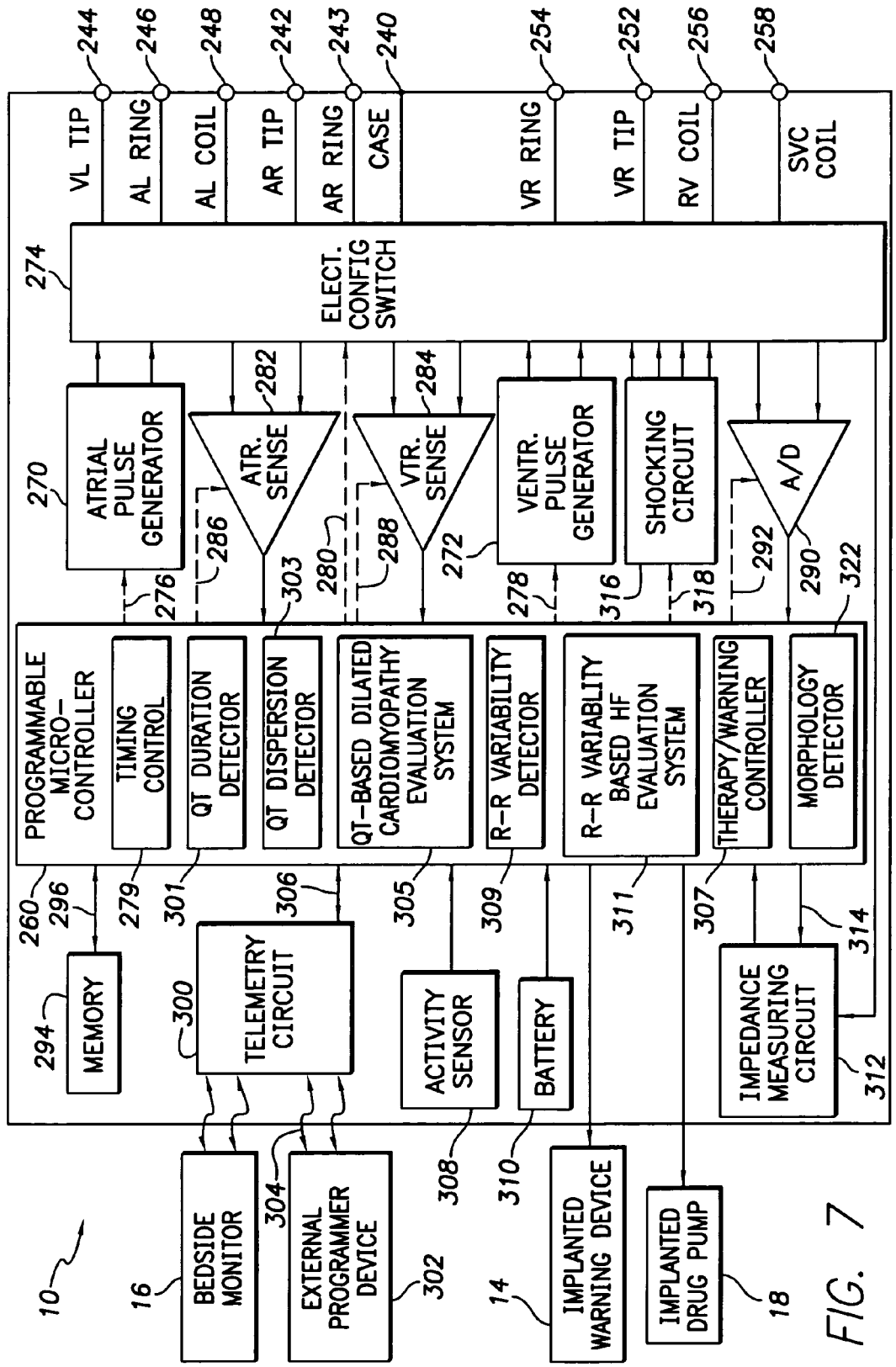
FIG. 7 is a functional block diagram of the pacer/ICD of FIG. 1, illustrating basic circuit elements that provide cardioversion, defibrillation and/or pacing stimulation in the heart and particularly illustrating components for detecting and distinguishing dilated cardiomyopathy and heart failure and for controlling delivery of therapy or warning signals in response thereto.

FIG. 1 illustrates an implantable medical system 8 capable of detecting and distinguishing dilated cardiomyopathy and heart failure and delivering appropriate warnings and possible therapy. More precisely, the device detects an increased risk in the medical condition(s) sufficient to warrant physician review. System 8 includes a pacer/ICD 10 or other cardiac stimulation device equipped with internal components for controlling the evaluation of cardiomyopathy and heart failure and for controlling the delivery of warnings and therapy in response thereto. More specifically, pacer/ICD 10 receives electrical cardiac signals from at least two cardiac pacing/sensing leads 12 implanted within the heart of the patient (shown stylistically in phantom lines) from which patient QT intervals and R-R intervals are derived. In FIG. 1, only two leads are shown. A more complete set of leads is shown in FIG. 7. Dilated cardiomyopathy and heart failure are detected and distinguished based on an analysis of the QT intervals and R-R intervals, using techniques to be described in detail below.

Warning signals are generated using either an internal warning device 14 or an external bedside monitor 16 so as to notify the patient of the possible onset of dilated cardiomyopathy and/or heart failure or to advise the patient of any significant progression thereof. Internal warning device 14 may be a vibrating device or a "tickle" voltage device that, in either case, provides perceptible stimulation to the patient to alert the patient of the need to consult a physician. The bedside monitor provides audible or visual alarm signals to alert the patient, as well as textual or graphic displays. In addition, once dilated cardiomyopathy and/or heart failure has been detected, diagnostic information is stored within the pacer/ICD for subsequent transmission to an external programmer (not shown in FIG. 1) for review by a physician or other medial professional. The physician may then prescribe any other appropriate therapies to address the condition. The physician may also adjust the operation of the pacer/ICD to activate, deactivate or otherwise control any therapies that are automatically applied. In addition, the bedside monitor may be directly networked with a centralized computing system for immediately notifying the physician of the onset of these or other medical condition. Networking techniques for use with implantable medical systems are set forth, for example, in U.S. Pat. No. 6,249,705 to Snell, entitled "Distributed Network System for Use with Implantable Medical Devices."

If dilated cardiomyopathy and/or heart failure is detected, appropriate therapy can then be delivered by the implantable system under the control of the pacer/ICD. For example, CRT therapy may be delivered to the heart of the patient using the ventricular leads in an effort to improve cardiac function. Additionally, or in the alternative, the implantable system may be equipped with a drug pump 18 capable of the delivering drug therapy in an attempt to address the condition. Discussions of possible medications are provided below. Drug dosages provided by an implantable drug pump may be titrated based on the severity of the condition.

Hence, FIG. 1 provides an overview of an implantable system for detecting and distinguishing dilated cardiomyopathy and heart failure, delivering appropriate warnings and therapy. Individual systems may be implemented that do not necessarily perform all of these functions. For example, systems may be implemented that detect dilated cardiomyopathy based on QT intervals but do not necessarily detect heart failure based on R-R variability. In addition, systems provided in accordance with the invention need not include all the components shown in FIG. 1. In many cases, for example, the system includes only the pacer/ICD and its leads, with therapy provided exclusively in the form of pacing/shocking therapy. Drug pumps and warning devices are not necessarily implanted. Other implementations may employ a bedside monitor for generating warning signals but no internal warning device. These are just a few exemplary embodiments. No attempt is made herein to describe all possible combinations of components that may be provided in accordance with the general principles of the invention.

Also, note that internal signal transmission lines provided for interconnecting the various implanted components are not specifically shown in FIG. 1. Wireless signal transmission may alternatively be employed. In addition, the particular locations and relative sizes of the implanted components shown in FIG. 1 are merely illustrative and may not necessarily correspond to actual locations and sizes.

Overview of Dilated Cardiomyopathy/Heart Failure Evaluation Techniques

Figure 2:
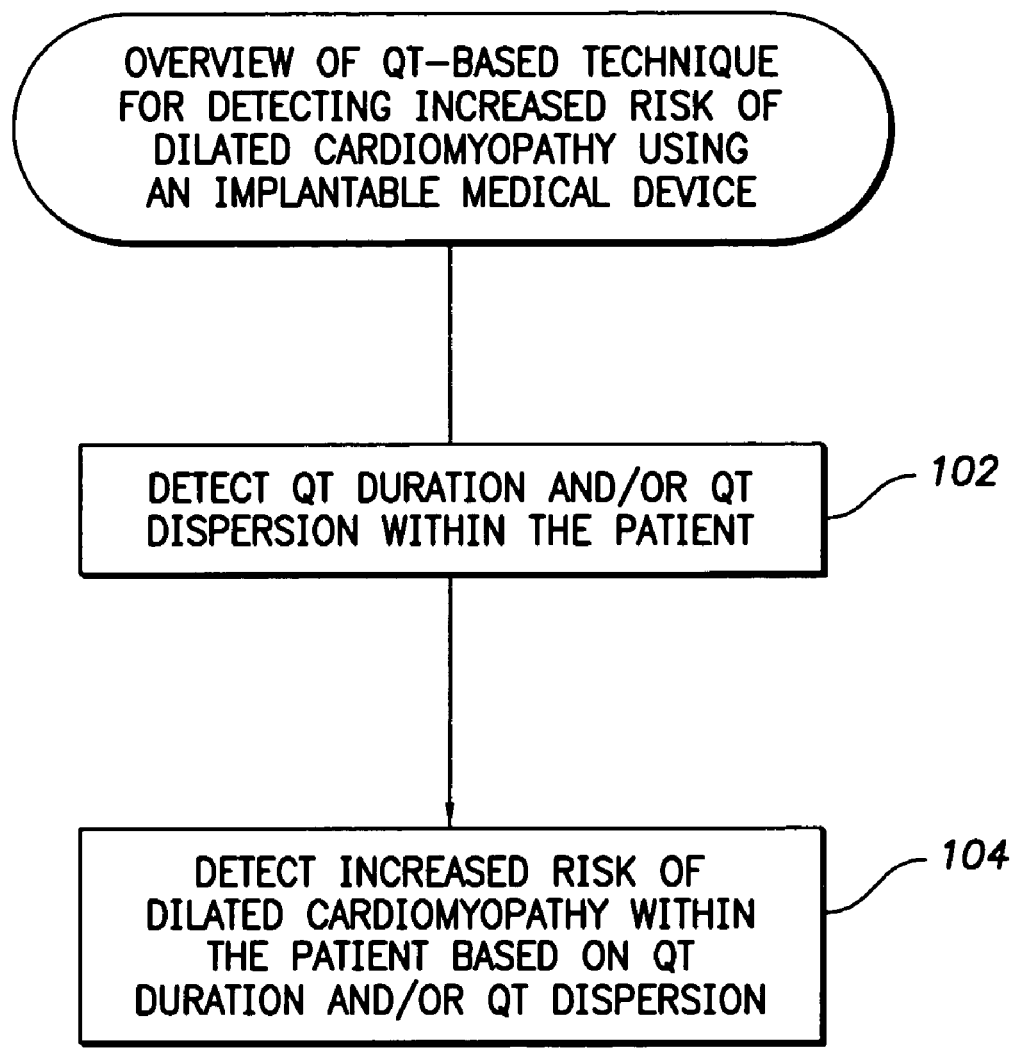
FIG. 2 is a flow diagram providing an overview of a technique for detecting an increased risk of dilated cardiomyopathy that may be performed by the system of FIG. 1.

FIG. 2 summarizes QT-based dilated cardiomyopathy evaluation techniques that may be performed using the system of FIG. 1. Beginning with step 102, the pacer/ICD detects values representative of QT duration and/or QT dispersion, using otherwise conventional techniques. As noted above, QT generally represents the time interval between a ventricular depolarization and a corresponding ventricular repolarization of the heart of the patient. In one specific example, the QT interval is defined as the time interval between the onset of the QRS-complex and the end of the T-wave. The onset of the QRS-complex and the end of the T-wave may be detected by comparing a time derivative of the detected cardiac signal against suitable threshold values. See, for example, techniques described in Alonso et al., "Dynamics of Ventricular Repolarization in Patients with Dilated Cardiomyopathy versus Healthy Subjects," Annals of Noninvasive Electrocardiology, 2005 April; 10(2)121-8. Preferably, cardiac signals are sensed by the pacer/ICD using different pairs of electrodes and hence slightly different values of the QT interval may be measured for each individual heartbeat. The pacer/ICD preferably averages the various individual QT interval values measured for a particular heartbeat together to yield a single value of "QT duration" for the particular heartbeat.

QT dispersion refers to the difference between the maximum detected QT interval and the minimum detected QT interval when the same QT interval is measured using different pairs of electrodes. For example, the length of the QT interval may be separately measured based on signals sensed (1) between a right ventricular (RV) tip electrode and the device housing; (2) between a left ventricular (LV) tip electrode and the device housing; and (3) between a right atrial (RA) tip electrode and the device can. For a given heartbeat, the longest QT interval may be found, for example, within the signals sensed RV tip-can (i.e. $QT_{RVtip\text{-}can}$); whereas the shortest QT interval may be found, for example, within the signals sensed LV tip-can (i.e. $QT_{LVtip\text{-}can}$). If so, the QT dispersion value for that particular heartbeat is then calculated as the difference between $QT_{RV\ tip\text{-}can}$ and $QT_{LVtip\text{-}can}$. Preferably, the cardiac signals of an individual heartbeat are sensed using a greater number of electrode pairs so as to generate more individual QT interval values for that heartbeat from which the QT dispersion value is then calculated. QT dispersion can, and usually does, vary from beat to beat. QT dispersion measured within IEGM signals is discussed, for example, in U.S. Patent Application 2004/0077962 of Kroll, entitled "System and Method for Monitoring Blood Glucose Levels Using an Implantable Medical Device." QT dispersion measured using signals detected using a Holter monitor is discussed, for example, within the Alonso et al. article.

Note that some measured QT intervals may represent bad data. This may be due to noise within the sensed signals, premature ventricular complexes, or other abnormalities. Accordingly, any anomalous QT intervals are preferably rejected. In one example, each new QT interval is compared against an average of some predetermined number of previously accepted QT intervals. If the new QT interval differs by more than ±10%, then the new QT interval is rejected. Whenever a QT interval is rejected for a particular heartbeat, then QT duration and QT dispersion value are not calculated for that heartbeat. As already explained, multiple QT intervals are measured for each heartbeat using different pairs of electrodes. Preferably, each new QT interval is compared only against the previous QT intervals measured using that same pair of electrodes. Whenever any individual QT interval is rejected as being bad data, the other QT intervals for that same heartbeat (detected using the other pairs of electrodes) are likewise rejected.

At step 104, the pacer/ICD then detects an increased risk of dilated cardiomyopathy within the patient based on the QT duration and/or QT dispersion values. Preferably, both parameters are employed. In general, the greater the QT duration and QT dispersion, the more likely the patient has dilated cardiomyopathy. See, again, the paper by Alonso et al. Studies reported therein indicate a significant increase in both QT duration and QT dispersion within patients with idiopathic dilated cardiomyopathy (IDC) verses healthy patients. In particular, a mean QT duration of 416.2±40.5 milliseconds (ms) was found in IDC patients versus 370.6±24.6 ms in healthy patients. A mean QT dispersion (QTd) of 54.4±30.4 ms was found in IDC patients versus 27.1±10.3 in healthy patients. Statistically significant differences were also found in the standard deviation (SD) of QTd, in the % peaks of QT corrected (i.e. QTc)>500 ms and in % peaks QTd>100 ms. The authors concluded that patients with dilated cardiomyopathy have increased QT duration, QT dispersion, and increased variability of QT dispersion. Hence, QT duration and QT dispersion may be used to detect an increased or elevated risk of dilated cardiomyopathy within patients. The other parameters (i.e. SD QTd, % peaks QTc, and % peaks QTd) may be assessed to supplement or confirm the detection of the increased risk of dilated cardiomyopathy.

A variety of techniques may be used at step 104 to detect the increased risk of dilated cardiomyopathy based on QT duration and/or QT dispersion. A particularly efficient histogram bin-based technique is discussed below in connection with FIGS. 4A and 4B. Other suitable techniques, however, may be used.

Thus, FIG. 2 summarizes the general technique for detecting an increased risk of dilated cardiomyopathy with a patient using a pacer/ICD based on QT duration and QT dispersion. In general, the greater the increase of QT duration and QT dispersion, the greater the likelihood that the patient indeed has dilated cardiomyopathy. However, the fact that QT duration and QT dispersion are elevated within a particular patient does not conclusively demonstrate that the patient definitely has dilated cardiomyopathy, but the increase is sufficient to warrant, at least, physician review. Preferably, changes in QT duration and QT dispersion are tracked and recorded within the pacer/ICD so that the physician may review the information and identify any trends. In addition, an increase in QT duration and QT dispersion are likely associated with changes in T-wave morphology. Such changes are also associated with an increased risk of arrhythmias. Accordingly, the detection of increased QT duration and QT dispersion values within the patient also preferably triggers a warning of an increased likelihood of arrhythmic events within the patent.

Figure 3:
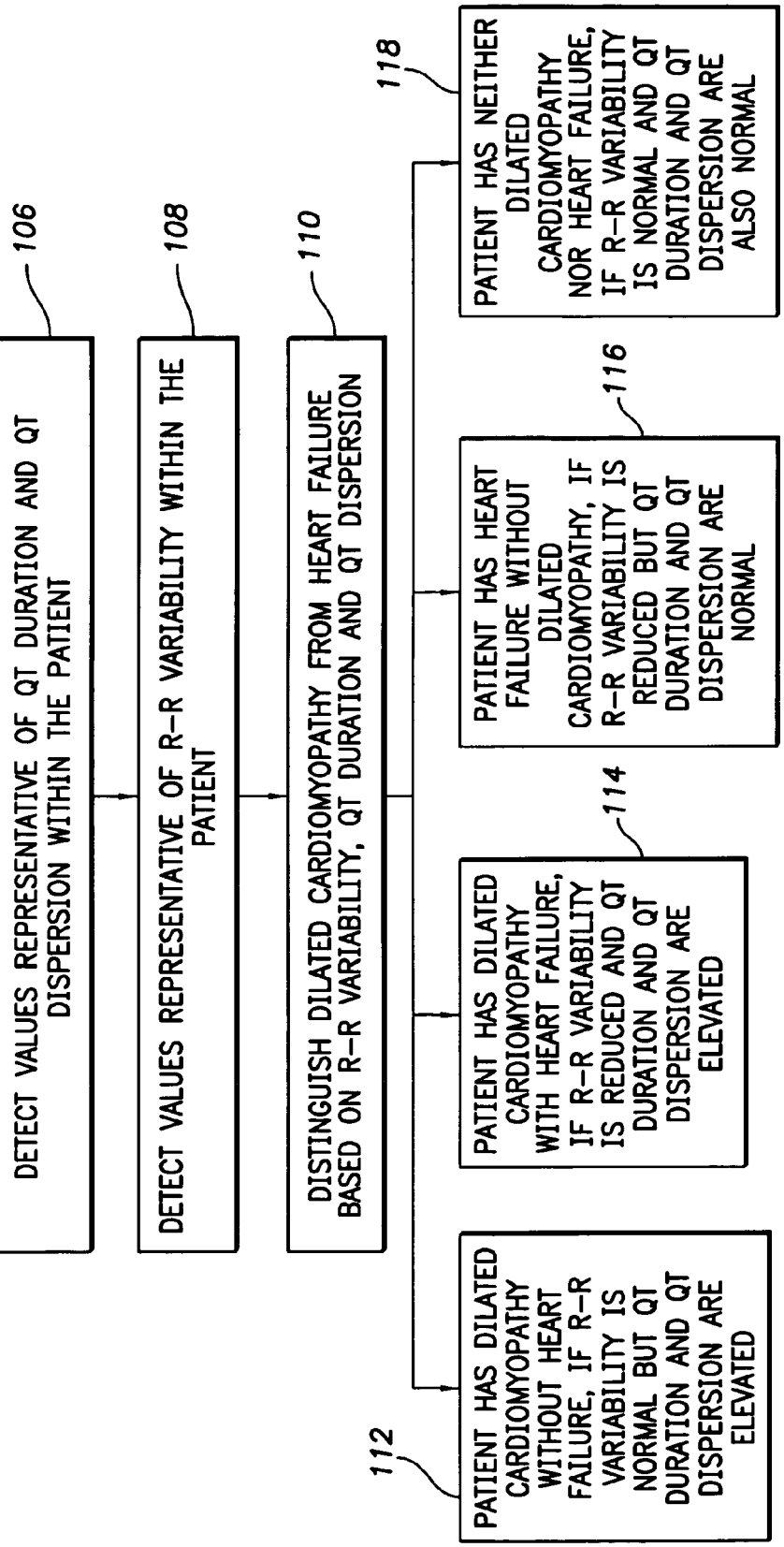
FIG. 3 is a flow diagram providing an overview of a technique for distinguishing between dilated cardiomyopathy and heart failure that may be performed by the system of FIG. 1.

Turning now to FIG. 3, a technique for distinguishing dilated cardiomyopathy from heart failure is summarized. At step 106, the pacer/ICD detects values representative of QT duration and QT dispersions are within the patient. At step 108, the pacer/ICD detects value representative of R-R variability. R-R variability may be detected, e.g., based on the standard deviation of normal RR intervals (SDNN). At step 110, the pacer/ICD then distinguishes dilated cardiomyopathy from heart failure based on R-R variability, QT duration and QT dispersion. In this regard, it is well established that heart failure is associated with a reduction of R-R variability due to compromised autonomous control of heart rhythm. As just explained, dilated cardiomyopathy is associated with an increase in QT duration and QT dispersion. Hence, if the heart rate variability of the patient is normal but QT dispersion and QT duration are elevated, the pacer/ICD thereby detects, at step 112, that the patient likely has dilated cardiomyopathy without associated heart failure, step 112. If R-R variability is reduced and QT dispersion and QT duration are both elevated, the pacer/ICD thereby detects, at step 114, then the patient likely has heart failure along with dilated cardiomyopathy. If R-R variability is reduced but QT dispersion and QT duration are both normal, the pacer/ICD thereby detects, at step 116, that the patient likely has heart failure without dilated cardiomyopathy. Finally, if R-R variability is normal and QT dispersion and QT duration are both likewise normal, the pacer/ICD thereby detects, at step 118, that the patient likely has neither heart failure nor dilated cardiomyopathy.

Thus, FIG. 3 summarizes the general technique for distinguishing dilated cardiomyopathy from heart failure using a pacer/ICD based on R-R-variability, QT duration and QT dispersion. As with the technique of FIG. 2, the technique of FIG. 3 does not necessarily provide for a conclusive diagnosis of the patient's condition but instead provides an indication to the physician of the likelihood of the condition to aid in diagnosis. Preferably, changes in R-R variability are also tracked and recorded within the pacer/ICD so that the physician may review the information, in conjunction with recorded QT information, to identify any trends.

Exemplary Histogram-Based Dilated Cardiomyopathy Evaluation Techniques

Figure 4B:
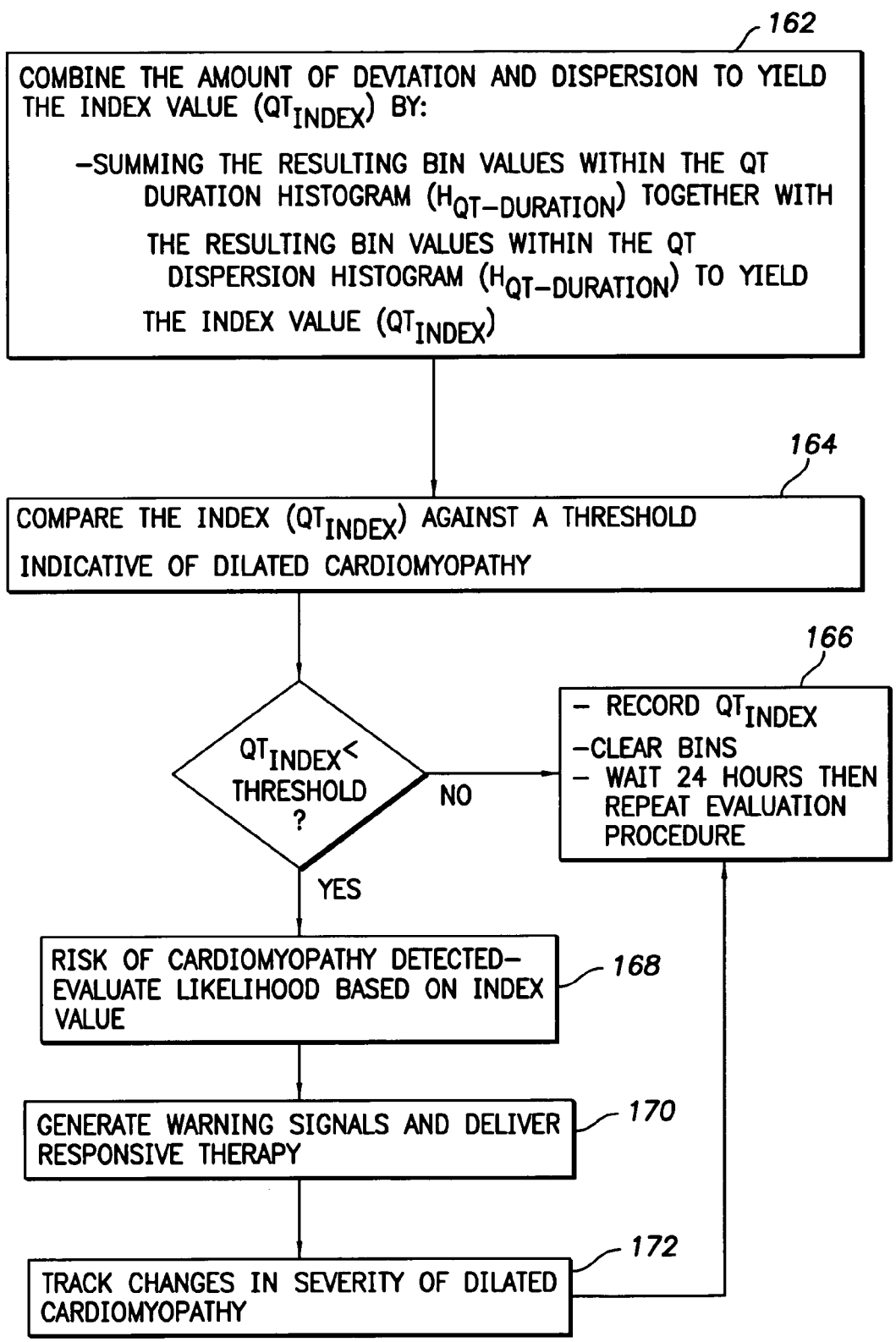

FIGS. 4A and 4B set forth a technique for QT-based technique for evaluating dilated cardiomyopathy, which exploits daily histograms. Initially, at step 152, the pacer/ICD detects QT duration and QT dispersion. This may be performed by: sensing the intracardiac electrogram (IEGM) of the patient; identifying QT intervals within the IEGM; and then calculating QT duration and QT dispersion based on the QT intervals. This corresponds to step 102 of FIG. 2. At step, 154, the pacer/ICD then determines QT duration and QT dispersion daily mean values by: generating a QT dispersion histogram ($H_{QT\text{-}DISPERSION}$) based on a plurality of QT dispersion values detected over one day; generating a QT duration histogram ($H_{QT\text{-}DURATION}$) based on a plurality of QT duration values detected over one day; and calculating a QT dispersion daily mean and a QT duration daily mean using the histograms.

Figure 5:
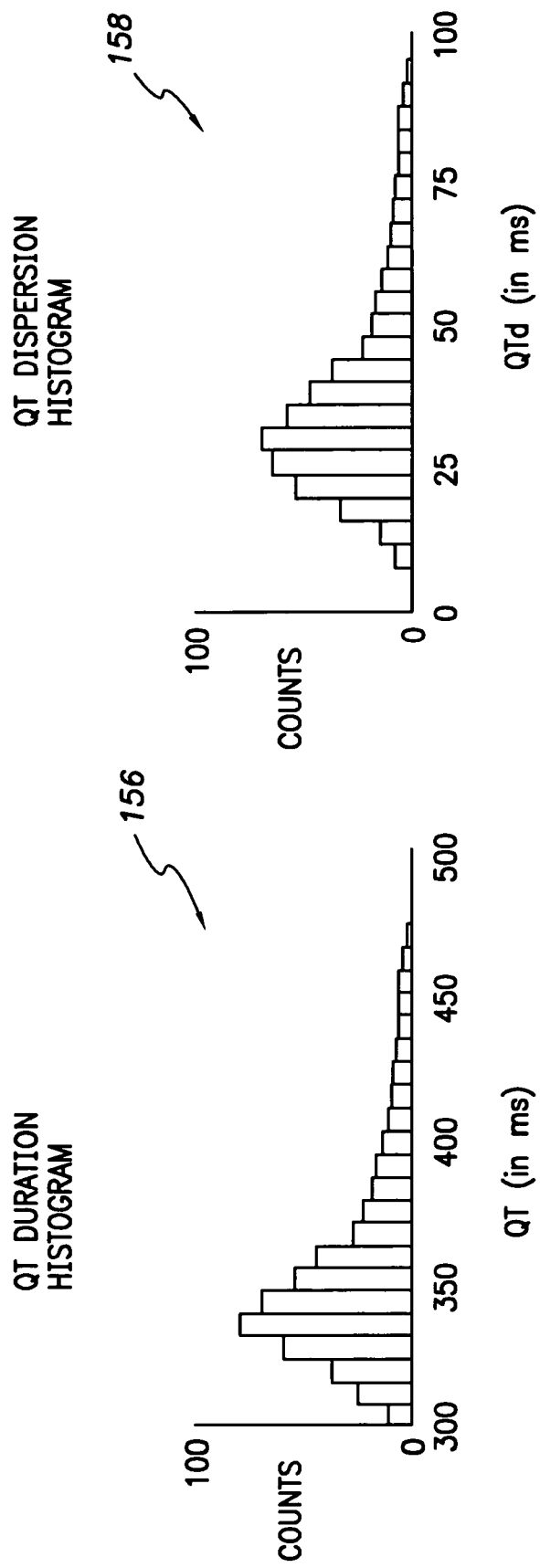
FIG. 5 sets forth exemplary QT duration and QT dispersion histograms exploited using the procedure of FIGS. 4A and 4B.

FIG. 5 illustrates an exemplary QT dispersion histogram ($H_{QT\text{-}DISPERSION}$) 156 and an exemplary QT duration histogram ($H_{QT\text{-}DURATION}$) 158. As can be seen, each histogram is composed of a series of bins representing a range of values. For each newly detected heartbeat, the pacer/ICD determines the QT duration and the QT dispersion then identifies the corresponding bin within each histogram. The corresponding bin is then incremented. This may be implemented by associating a numerical counter with each bin. For example, whenever a QT dispersion value is detected within range associated with bin #3, then the counter of bin #3 is incremented. By utilizing bins, the pacer/ICD need not record each QT duration and QT dispersion value. Rather, the pacer/ICD merely maintains a counter value for each bin, thus saving memory and processing resources. Once per day, the QT duration mean and the QT dispersion mean are calculated based on the counter values, then the bins are cleared, i.e. the counters are reset to zero. The daily QT duration mean and QT dispersion mean values may be stored elsewhere in memory for trending purposes. Note that the histograms of FIG. 5 sets forth hypothetical exemplary data provide merely to illustrate this feature of the invention and should not be construed as representing actual clinically-obtained data.

Returning to FIGS. 4A and 4B, at step 160, the pacer/ICD then quantifies the deviation in QT duration and QT dispersion from their respective daily means. This may be performed by: subtracting the QT dispersion daily mean from each bin value in the QT dispersion histogram ($H_{QT\text{-}DISPERSION}$); subtracting the QT duration daily mean from each bin value in the QT duration histogram ($H_{QT\text{-}DURATION}$) and multiplying each of the bin values in the QT duration histogram ($H_{QT\text{-}DURATION}$) by a corresponding QT duration histogram ($H_{QT\text{-}DURATION}$) bin count; and subtracting the QT dispersion daily mean from each bin value in the QT dispersion histogram ($H_{QT\text{-}DISPERSION}$) and multiplying each of the bin values in the QT dispersion histogram ($H_{QT\text{-}DISPERSION}$) by a corresponding QT dispersion histogram ($H_{QT\text{-}DISPERSION}$) bin count. Next, at step 162, the pacer/ICD combines the amount of deviation and dispersion to yield an index value ($QT_{INDEX}$) by summing the resulting bin values within the QT duration histogram ($H_{QT\text{-}DURATION}$) together with the resulting bin values within the QT dispersion histogram ($H_{QT\text{-}DURATION}$). At step 164, the pacer/ICD then compares $QT_{INDEX}$ against a predetermined threshold indicative of an elevated risk of dilated cardiomyopathy. The threshold may be set, for example, based on nominal values for the particular patient. That is, following device implant within a patient known not to have dilated cardiomyopathy, the pacer/ICD determines and records a nominal $QT_{INDEX}$ value. The threshold is then set based on the nominal value by setting it, e.g., to a value 25% greater than the nominal value. 25% is merely an exemplary value. Otherwise routine studies and experiments may be performed to determine a suitable percentage value for use in detecting an increased risk of dilated cardiomyopathy within patients. Preferably, the threshold is adjustable by the physician. Steps 154 and 160-164 of FIGS. 4A and 4B generally correspond to step 104 of FIG. 2.

So long as the index remains below the threshold, then step 166 is performed wherein diagnostic data is recorded (such as the latest value of the index), the bins are cleared and the pacer/ICD then waits 24 hours before repeating the evaluation procedure. If, however, the index exceeds the threshold, then a risk of cardiomyopathy is thereby detected at step 168. The degree of risk may be evaluated based on the index, i.e. the higher the index the greater the risk. Warning signals are then generated at step 170. To prevent temporary anomalous QT values from triggering a false positive detection, the pacer/ICD may be configured to generate a warning only if the index exceeds the threshold for some predetermined number of days. In addition, in some implementations, the device may be equipped to automatically deliver therapy in response to a substantial likelihood of dilated cardiomyopathy. For example, pacing therapy appropriate for addressing dilated cardiomyopathy may be initiated. In particular, see U.S. Pat. No. 5,340,361 to Sholder, entitled "Implantable Pacemaker Having Adaptive AV Interval Adoptively Shortened to Assure Ventricular Pacing", which sets forth pacing techniques particularly adapted for use by patients suffering from a cardiomyopathy in order to improve cardiac output.

In addition, if a drug pump is provided with medications appropriate for dilated cardiomyopathy, then such medications can be dispensed. Implantable drug pumps are discussed in U.S. Pat. No. 5,328,460 to Lord, et al., entitled "Implantable Medication Infusion Pump Including Self-Contained Acoustic Fault Detection Apparatus." Routine experimentation may be employed to identify medications for treatment of dilated cardiomyopathy that are safe and effective for use in connection with an implantable drug pump. Medication that may be appropriate include, e.g., angiotensin-converting enzyme (ACE) inhibitors and beta-blockers. As can be appreciated, therapy should only be automatically delivered if there is a substantial likelihood that the patient has dilated cardiomyopathy as determined, e.g., based on highly elevated QT duration and QT dispersion values, preferably in combination with other corroborating parameters.

At step 172, the pacer/ICD may also track changes in the severity of dilated cardiomyopathy within the patient based, e.g. on changes in the index value over time. Any significant progression in the severity of the condition may trigger additionally warnings or may trigger therapy that is more aggressive.

What have been described are various techniques for detecting and distinguishing dilated cardiomyopathy. For the sake of completeness, an exemplary pacer/ICD will now be described, which includes exemplary components for implementing the techniques of FIGS. 2-5. It should be understood though that the techniques may be implanted within other implantable devices. Alternatively, the techniques may be implemented within external devices (such as within a bedside monitor) based on information relayed from an implanted device.

Exemplary Pacer/ICD

Figure 6:
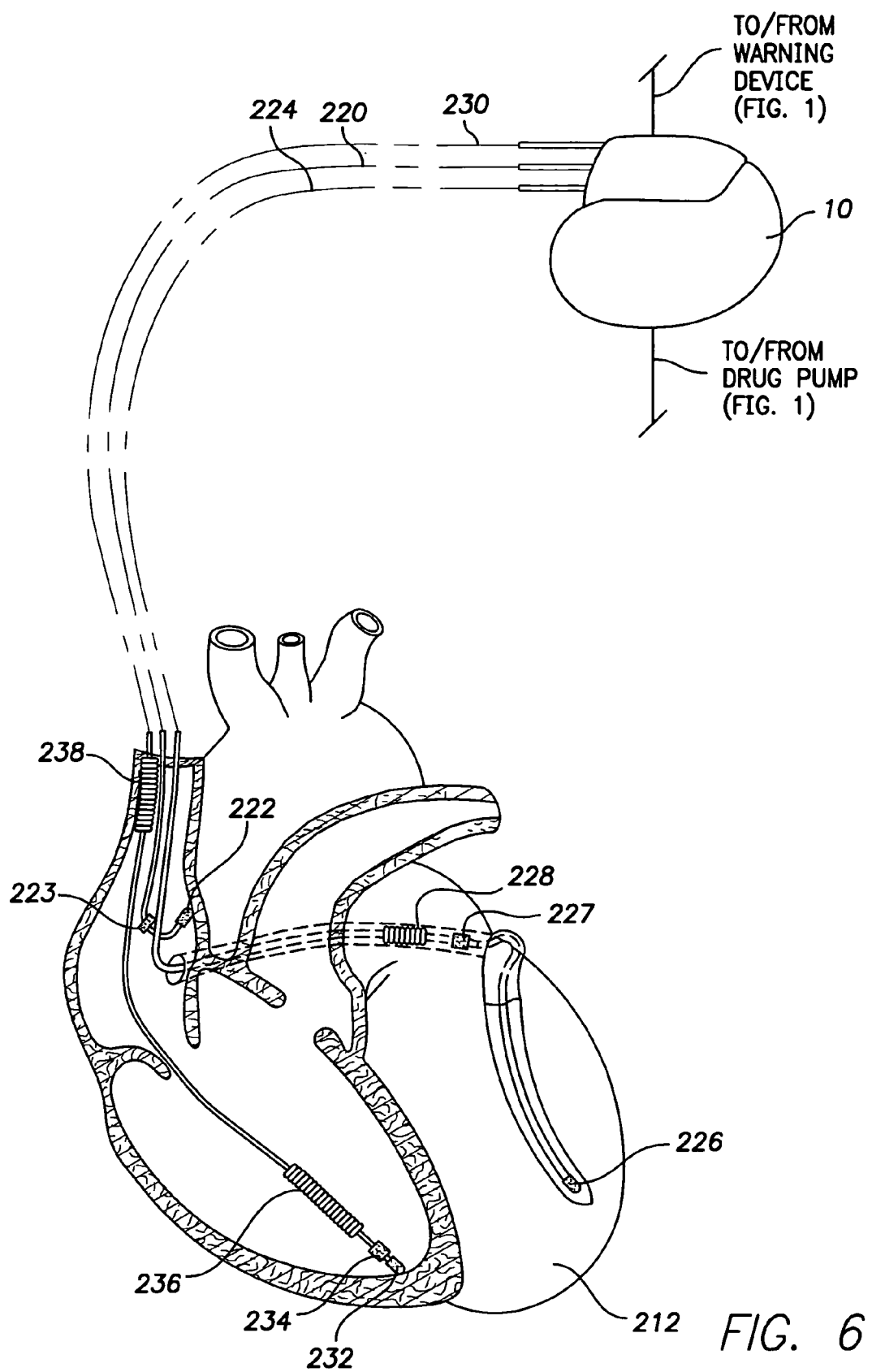
FIG. 6 is a simplified, partly cutaway view, illustrating the pacer/ICD of FIG. 1 along with at set of three exemplary leads implanted into the heart of the patient.

FIG. 6 provides a simplified block diagram of pacer/ICD 10 of FIG. 1, which is a dual-chamber stimulation device capable of treating both fast and slow arrhythmias with stimulation therapy, including cardioversion, defibrillation, and pacing stimulation, as well as capable of detecting and distinguishing dilated cardiomyopathy and heart failure and controlling the delivery of therapy and warnings in response thereto.

To provide atrial chamber pacing stimulation and sensing, pacer/ICD 10 is shown in electrical communication with a heart 212 by way of a right atrial lead 220 having an atrial tip electrode 222 and an atrial ring electrode 223 implanted in the atrial appendage. Pacer/ICD 10 is also in electrical communication with the heart by way of a right ventricular lead 230 having, in this embodiment, a right ventricular tip electrode 232, a right ventricular ring electrode 234, a right ventricular coil electrode 236, and a superior vena cava (SVC) coil electrode 238. Typically, the right ventricular lead 230 is transvenously inserted into the heart so as to place the RV coil electrode 236 in the right ventricular apex, and the SVC coil electrode 238 in the superior vena cava. Accordingly, the right ventricular lead is capable of receiving cardiac signals, and delivering stimulation in the form of pacing and shock therapy to the right ventricle.

To sense left atrial and left ventricular cardiac signals and to provide left chamber pacing therapy, pacer/ICD 10 is coupled to a "coronary sinus" lead 224 designed for placement in the "coronary sinus region" via the coronary sinus os for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus. Accordingly, an exemplary coronary sinus lead 224 is designed to receive atrial and ventricular cardiac signals and to deliver left ventricular pacing therapy using at least a left ventricular tip electrode 226, left atrial pacing therapy using at least a left atrial ring electrode 227, and shocking therapy using at least a left atrial coil electrode 228.

With this configuration, biventricular pacing can be performed. Although only three leads are shown in FIG. 6, it should also be understood that additional stimulation leads (with one or more pacing, sensing and/or shocking electrodes) may be used in order to efficiently and effectively provide pacing stimulation to the left side of the heart or atrial cardioversion and/or defibrillation.

A simplified block diagram of internal components of pacer/ICD 10 is shown in FIG. 7. While a particular pacer/ICD is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation as well as providing for the aforementioned cardiomyopathy and heart failure detection and therapy. The housing 240 for pacer/ICD 10, shown schematically in FIG. 7, is often referred to as the "can", "case" or "case electrode" and may be programmably selected to act as the return electrode for all "unipolar" modes. The housing 240 may further be used as a return electrode alone or in combination with one or more of the coil electrodes, 228, 236 and 238, for shocking purposes. The housing 240 further includes a connector (not shown) having a plurality of terminals, 242, 243, 244, 246, 248, 252, 254, 256 and 258 (shown schematically and, for convenience, the names of the electrodes to which they are connected are shown next to the terminals). As such, to achieve right atrial sensing and pacing, the connector includes at least a right atrial tip terminal ($A_R$ TIP) 242 adapted for connection to the atrial tip electrode 222 and a right atrial ring ($A_R$ RING) electrode 243 adapted for connection to right atrial ring electrode 223. To achieve left chamber sensing, pacing and shocking, the connector includes at least a left ventricular tip terminal ($V_L$ TIP) 244, a left atrial ring terminal ($A_L$ RING) 246, and a left atrial shocking terminal ($A_L$ COIL) 248, which are adapted for connection to the left ventricular ring electrode 226, the left atrial tip electrode 227, and the left atrial coil electrode 228, respectively. To support right chamber sensing, pacing and shocking, the connector further includes a right ventricular tip terminal ($V_R$ TIP) 252, a right ventricular ring terminal ($V_R$ RING) 254, a right ventricular shocking terminal ($R_V$ COIL) 256, and an SVC shocking terminal (SVC COIL) 258, which are adapted for connection to the right ventricular tip electrode 232, right ventricular ring electrode 234, the RV coil electrode 236, and the SVC coil electrode 238, respectively.

At the core of pacer/ICD 10 is a programmable microcontroller 260, which controls the various modes of stimulation therapy. As is well known in the art, the microcontroller 260 (also referred to herein as a control unit) typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 260 includes the ability to process or monitor input signals (data) as controlled by a program code stored in a designated block of memory. The details of the design and operation of the microcontroller 260 are not critical to the invention. Rather, any suitable microcontroller 260 may be used that carries out the functions described herein. The use of microprocessor-based control circuits for performing timing and data analysis functions are well known in the art.

As shown in FIG. 7, an atrial pulse generator 270 and a ventricular pulse generator 272 generate pacing stimulation pulses for delivery by the right atrial lead 220, the right ventricular lead 230, and/or the coronary sinus lead 224 via an electrode configuration switch 274. It is understood that in order to provide stimulation therapy in each of the four chambers of the heart, the atrial and ventricular pulse generators, 270 and 272, may include dedicated, independent pulse generators, multiplexed pulse generators or shared pulse generators. The pulse generators, 270 and 272, are controlled by the microcontroller 260 via appropriate control signals, 276 and 278, respectively, to trigger or inhibit the stimulation pulses.

The microcontroller 260 further includes timing control circuitry (not separately shown) used to control the timing of such stimulation pulses (e.g., pacing rate, atrio-ventricular (AV) delay, atrial interconduction (A-A) delay, or ventricular interconduction (V-V) delay, etc.) as well as to keep track of the timing of refractory periods, blanking intervals, noise detection windows, evoked response windows, alert intervals, marker channel timing, etc., which is well known in the art. Switch 274 includes a plurality of switches for connecting the desired electrodes to the appropriate I/O circuits, thereby providing complete electrode programmability. Accordingly, the switch 274, in response to a control signal 280 from the microcontroller 260, determines the polarity of the stimulation pulses (e.g., unipolar, bipolar, combipolar, etc.) by selectively closing the appropriate combination of switches (not shown) as is known in the art.

Atrial sensing circuits 282 and ventricular sensing circuits 284 may also be selectively coupled to the right atrial lead 220, coronary sinus lead 224, and the right ventricular lead 230, through the switch 274 for detecting the presence of cardiac activity in each of the four chambers of the heart. Accordingly, the atrial (ATR. SENSE) and ventricular (VTR. SENSE) sensing circuits, 282 and 284, may include dedicated sense amplifiers, multiplexed amplifiers or shared amplifiers. The switch 274 determines the "sensing polarity" of the cardiac signal by selectively closing the appropriate switches, as is also known in the art. In this way, the clinician may program the sensing polarity independent of the stimulation polarity. Each sensing circuit, 282 and 284, preferably employs one or more low power, precision amplifiers with programmable gain and/or automatic gain control and/or automatic sensitivity control, bandpass filtering, and a threshold detection circuit, as known in the art, to selectively sense the cardiac signal of interest. The outputs of the atrial and ventricular sensing circuits, 282 and 284, are connected to the microcontroller 260 which, in turn, are able to trigger or inhibit the atrial and ventricular pulse generators, 270 and 272, respectively, in a demand fashion in response to the absence or presence of cardiac activity in the appropriate chambers of the heart.

For arrhythmia detection, pacer/ICD 10 utilizes the atrial and ventricular sensing circuits, 282 and 284, to sense cardiac signals to determine whether a rhythm is physiologic or pathologic. As used in this section "sensing" is reserved for the noting of an electrical signal, and "detection" is the processing of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the microcontroller 260 by comparing them to a predefined rate zone limit (i.e., bradycardia, normal, atrial tachycardia, atrial fibrillation, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, antitachycardia pacing, cardioversion shocks or defibrillation shocks).

Cardiac signals are also applied to the inputs of an analog-to-digital (A/D) data acquisition system 290. The data acquisition system 290 is configured to acquire intracardiac electrogram signals, convert the raw analog data into a digital signal, and store the digital signals for later processing and/or telemetric transmission to an external device 302. The data acquisition system 290 is coupled to the right atrial lead 220, the coronary sinus lead 224, and the right ventricular lead 230 through the switch 274 to sample cardiac signals across any pair of desired electrodes. The microcontroller 260 is further coupled to a memory 294 by a suitable data/address bus 296, wherein the programmable operating parameters used by the microcontroller 260 are stored and modified, as required, in order to customize the operation of pacer/ICD 10 to suit the needs of a particular patient. Such operating parameters define, for example, pacing pulse amplitude or magnitude, pulse duration, electrode polarity, rate, sensitivity, automatic features, arrhythmia detection criteria, and the amplitude, waveshape and vector of each shocking pulse to be delivered to the patient's heart within each respective tier of therapy. Other pacing parameters include base rate, rest rate and circadian base rate.

Advantageously, the operating parameters of the implantable pacer/ICD 10 may be non-invasively programmed into the memory 294 through a telemetry circuit 300 in telemetric communication with the external device 302, such as a programmer, transtelephonic transceiver or a diagnostic system analyzer. The telemetry circuit 300 is activated by the microcontroller by a control signal 306. The telemetry circuit 300 advantageously allows intracardiac electrograms and status information relating to the operation of pacer/ICD 10 (as contained in the microcontroller 260 or memory 294) to be sent to the external device 302 through an established communication link 304. Pacer/ICD 10 further includes an accelerometer or other physiologic sensor 308, commonly referred to as a "rate-responsive" sensor because it is typically used to adjust pacing stimulation rate according to the exercise state of the patient. However, the physiological sensor 308 may further be used to detect changes in cardiac output, changes in the physiological condition of the heart, or diurnal changes in activity (e.g., detecting sleep and wake states) and to detect arousal from sleep. Accordingly, the microcontroller 260 responds by adjusting the various pacing parameters (such as rate, AV Delay, V-V Delay, etc.) at which the atrial and ventricular pulse generators, 270 and 272, generate stimulation pulses. While shown as being included within pacer/ICD 10, it is to be understood that the physiologic sensor 308 may also be external to pacer/ICD 10, yet still be implanted within or carried by the patient. A common type of rate responsive sensor is an activity sensor incorporating an accelerometer or a piezoelectric crystal, which is mounted within the housing 240 of pacer/ICD 10. Other types of physiologic sensors are also known, for example, sensors that sense the oxygen content of blood, respiration rate and/or minute ventilation, pH of blood, ventricular gradient, etc.

The pacer/ICD additionally includes a battery 310, which provides operating power to all of the circuits shown in FIG. 7. The battery 310 may vary depending on the capabilities of pacer/ICD 10. If the system only provides low voltage therapy, a lithium iodine or lithium copper fluoride cell may be utilized. For pacer/ICD 10, which employs shocking therapy, the battery 310 must be capable of operating at low current drains for long periods, and then be capable of providing high-current pulses (for capacitor charging) when the patient requires a shock pulse. The battery 310 must also have a predictable discharge characteristic so that elective replacement time can be detected. Accordingly, pacer/ICD 10 is preferably capable of high voltage therapy and appropriate batteries.

As further shown in FIG. 7, pacer/ICD 10 is shown as having an impedance measuring circuit 312 which is enabled by the microcontroller 260 via a control signal 314. Uses of the an impedance measuring circuit include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves, etc. The impedance measuring circuit 120 is advantageously coupled to the switch 74 so that any desired electrode may be used.

In the case where pacer/ICD 10 is intended to operate as an implantable cardioverter/defibrillator (ICD) device, it detects the occurrence of an arrhythmia, and automatically applies an appropriate electrical shock therapy to the heart aimed at terminating the detected arrhythmia. To this end, the microcontroller 260 further controls a shocking circuit 316 by way of a control signal 318. The shocking circuit 316 generates shocking pulses of low (up to 0.5 joules), moderate (0.5-10 joules) or high energy (11 to 40 joules), as controlled by the microcontroller 260. Such shocking pulses are applied to the heart of the patient through at least two shocking electrodes, and as shown in this embodiment, selected from the left atrial coil electrode 228, the RV coil electrode 236, and/or the SVC coil electrode 238. The housing 240 may act as an active electrode in combination with the RV electrode 236, or as part of a split electrical vector using the SVC coil electrode 238 or the left atrial coil electrode 228 (i.e., using the RV electrode as a common electrode). Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5-40 joules), delivered asynchronously (since R-waves may be too disorganized), and pertaining exclusively to the treatment of fibrillation. Accordingly, the microcontroller 260 is capable of controlling the synchronous or asynchronous delivery of the shocking pulses.

Microcontroller 260 also includes various components directed to the controlling the detection and treatment of dilated cardiomyopathy and heart failure. More specifically, the microcontroller includes a QT duration detector 301 operative to detect the duration of the QT interval of each heartbeat. A QT dispersion detector 303 detects the dispersion of the QT intervals. A dilated cardiomyopathy evaluation system 305 operates, at least, to detect an increased risk of dilated cardiomyopathy within the patient based on Qt duration and QT dispersion. A therapy/warning controller 307 operates to generate warning signals and control the delivery of automatic therapy, if any, in response to the detection of the increased risk of dilated cardiomyopathy. Warning signals may be delivered directly to the patient via implanted warning device 14, if provided, or via bedside monitor 16, using telemetry circuit 300. Additionally, an R-R variability detector 309 and an R-R variability-based heart failure evaluation system 311 may be provided to detect an increased risk of heart failure based on reduced R-R variability. Based on information provided by dilated cardiomyopathy evaluation system 305 and R-R variability-based heart failure evaluation system 311, the microcontroller can additionally distinguish between dilated cardiomyopathy and heart failure, within patients in circumstances where the patient has one of the conditions but not both. If the device is equipped to detect heart failure, then therapy/warning controller 307 also preferably operates to generate warning signals and control the delivery of automatic therapy, if any, in response to the detection of heart failure.

Depending upon the particular implementation, the various components of the microcontroller may be implemented as separate software modules. The modules may be combined to permit a single module to perform multiple functions. In addition, although shown as being sub-components of the microcontroller, some or all of these components may be implemented separately from the microcontroller.

Principles of the invention may be exploiting using other implantable systems or in accordance with other techniques. Indeed, general principles invention may be exploited with systems not incorporating pacemakers or ICDs but instead incorporating other implantable medical devices. As can be appreciated, a wide variety of specific implementations may be developed consistent with the principles of the invention and no attempt is made herein to describe or enumerate all such possible implementations. Thus, while the invention has been described with reference to particular embodiments, modifications can be made thereto without departing from the scope of the invention. Note also that the term "including" as used herein is intended to be inclusive, i.e. "including but not limited to."

What is claimed is:

1. A method for detecting an increased risk of dilated cardiomyopathy within a patient for use by an implantable medical device for implant within the patient, the method comprising:

detecting values representative of both QT duration and QT dispersion within the patient using the implantable medical device;

generating a QT dispersion histogram ($H_{QT\text{-}dispersion}$) based on a plurality of QT dispersion values detected over one day;

generating a QT duration histogram ($H_{QT\text{-}duration}$) based on a plurality of QT duration values detected over one day; and calculating a QT dispersion daily mean and a QT duration daily mean using the histograms calculating an index ($QT_{INDEX}$) representative of an amount of deviation in QT duration and in QT dispersion values from their respective daily means as follows:

subtracting the QT dispersion daily mean from each bin value in the QT dispersion histogram ($H_{QT\text{-}dispersion}$);

subtracting the QT duration daily mean from each bin value in the QT duration histogram ($H_{QT\text{-}duration}$) and multiplying each of the bin values in the QT duration histogram ($H_{QT\text{-}duration}$) by a corresponding QT duration histogram ($H_{QT\text{-}duration}$) bin count; and subtracting the QT dispersion daily mean from each bin value in the QT dispersion histogram ($H_{QT\text{-}dispersion}$) and multiplying each of the bin values in the QT dispersion histogram ($H_{QT\text{-}dispersion}$) by a corresponding QT dispersion histogram ($H_{QT\text{-}dispersion}$) bin count; and combining the amount of deviation and dispersion to yield the index value ($QT_{INDEX}$); and detecting an increased risk of dilated cardiomyopathy within the patient by comparing the index ($QT_{INDEX}$) against a threshold ($DC_{THRESHOLD}$) indicative of dilated cardiomyopathy.

2. The method of claim 1 wherein combining the amount of deviation and dispersion to yield the index value ($QT_{INDEX}$) includes:

summing the resulting bin values within the QT duration histogram ($H_{QT\text{-}duration}$) together with the resulting bin values within the QT dispersion histogram ($H_{QT\text{-}duration}$) to yield the index value ($QT_{INDEX}$).

3. The method of claim 1 further including evaluating the severity of dilated cardiomyopathy, if present within the patient, based on the index value ($QT_{INDEX}$).

4. The method of claim 3 further including tracking changes in the severity of dilated cardiomyopathy by detecting differences between index values ($QT_{INDEX}$) generated based on QT data collected at different times.

5. The method of claim 1 further comprising controlling delivery of therapy by the implantable medical device in response to the detection of an increased risk of dilated cardiomyopathy.

6. The method of claim 5 wherein the implantable medical device is capable of delivering cardiac pacing and wherein controlling delivery of therapy comprises controlling the delivery of pacing therapy to the heart of the patient in a manner effective to address dilated cardiomyopathy.

7. The method of claim 5 wherein an implantable drug pump is provided and wherein controlling delivering therapy comprises delivering medications effective to address dilated cardiomyopathy to the patient using the drug pump.

8. The method of claim 1 wherein an implantable warning device is provided and wherein the method further comprises generating warning signals using the implantable warning device based on the detection of an increased risk of dilated cardiomyopathy.

9. The method of claim 1 wherein an external warning device is provided and wherein the method further comprises transmitting appropriate signals to the external warning device indicative of an increased risk of dilated cardiomyopathy.

10. The method of claim 1 further comprising controlling storage of diagnostic information indicative of the increased risk of dilated cardiomyopathy.

\* \* \* \* \*